(12) United States Patent  
Pastyr et al.

(10) Patent No.: US 6,188,748 B1  
(45) Date of Patent: Feb. 13, 2001

(54) CONTOUR COLLIMATOR FOR RADIOTHERAPY

(75) Inventors: Otto Pastyr, Laimen; Wolfgang Schlegel, Heidelberg; Karl-Heinz Hover, Sinsheim; Wolfgang Maier-Borst, Dossenheim, all of (DE)

(73) Assignee: Deutsches Krebsforschungszentrum Stiftung des Offentlichen Rechts, Heidelberg (DE)

( * ) Notice: Under 35 U.S.C. 154(b), the term of this patent shall be extended for 0 days.

(21) Appl. No.: 09/043,951

(22) PCT Filed: Oct. 1, 1996

(86) PCT No.: PCT/DE96/01892  
§ 371 Date: May 29, 1998  
§ 102(e) Date: May 29, 1998

(87) PCT Pub. No.: WO97/13255  
PCT Pub. Date: Apr. 10, 1997

(30) Foreign Application Priority Data

Oct. 2, 1995 (DE) .............................................. 195 36 804

(51) Int. Cl.[7] ...................................................... G21K 1/04  
(52) U.S. Cl. .............................. 378/151; 378/65; 378/152  
(58) Field of Search .................................. 378/65, 64, 68, 378/145, 147, 149, 158, 151, 152, 153

(56) References Cited

U.S. PATENT DOCUMENTS

| 4,313,349 | 2/1982 | Heitman . |
| 4,868,844 | * 9/1989 | Nunan ................................... 378/152 |
| 5,160,847 | * 11/1992 | Leavitt et al. .................... 378/152 X |
| 5,555,283 | 9/1996 | Shiu et al. . |
| 5,889,834 | * 3/1999 | Vilsmeier et al. .................... 378/147 |

FOREIGN PATENT DOCUMENTS

| 0 387 921 A2 | 9/1990 | (EP) . |
| 2 485 790 | 12/1981 | (FR) . |
| WO94/29882 | 12/1994 | (WO) . |

\* cited by examiner

*Primary Examiner*—David P. Porta  
(74) *Attorney, Agent, or Firm*—Steven J. Hultquist; William A. Barrett

(57) ABSTRACT

A contour collimator has a plurality of plate-shaped diaphragm elements movably arranged with respect to each other in a guiding block to form a contour diaphragm for a radiation beam emitted by a radiation source towards the collimator, and at least one drive for moving the diaphragm elements. A drive is associated with each diaphragm element with the drives of a group of diaphragm elements being substantially adjacent, and a driving transmission arranged between each drive and the associated diaphragm element.

19 Claims, 6 Drawing Sheets

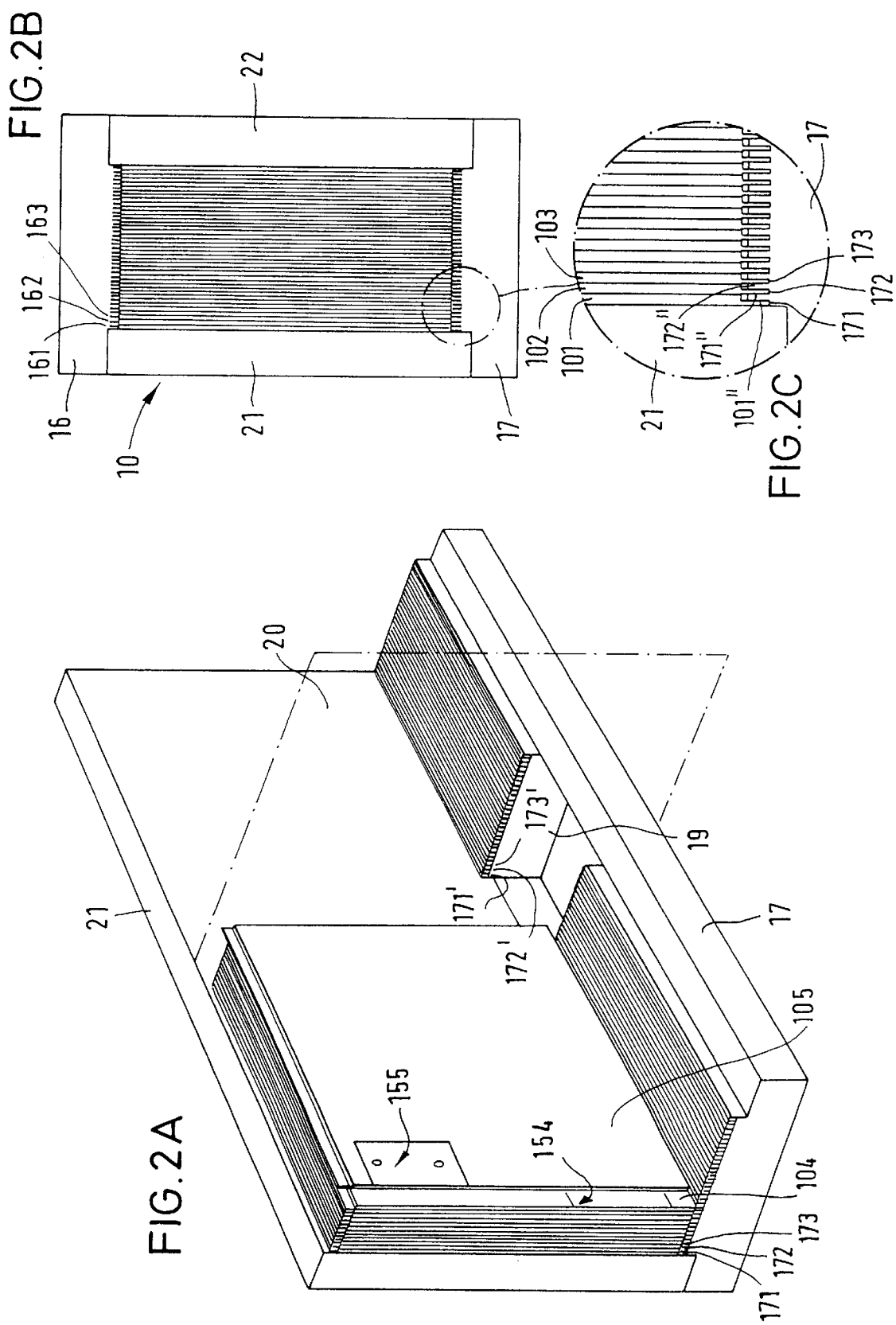

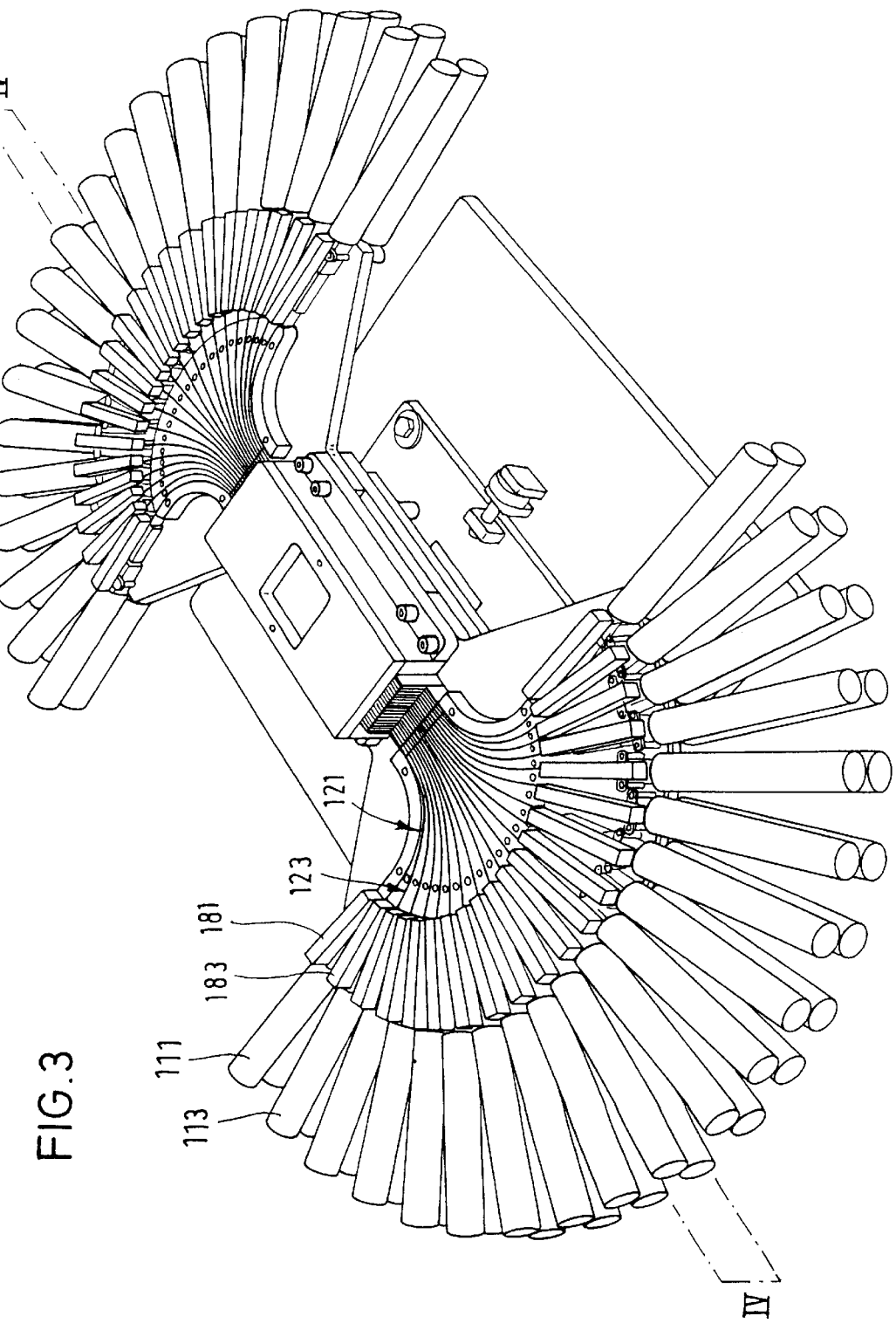

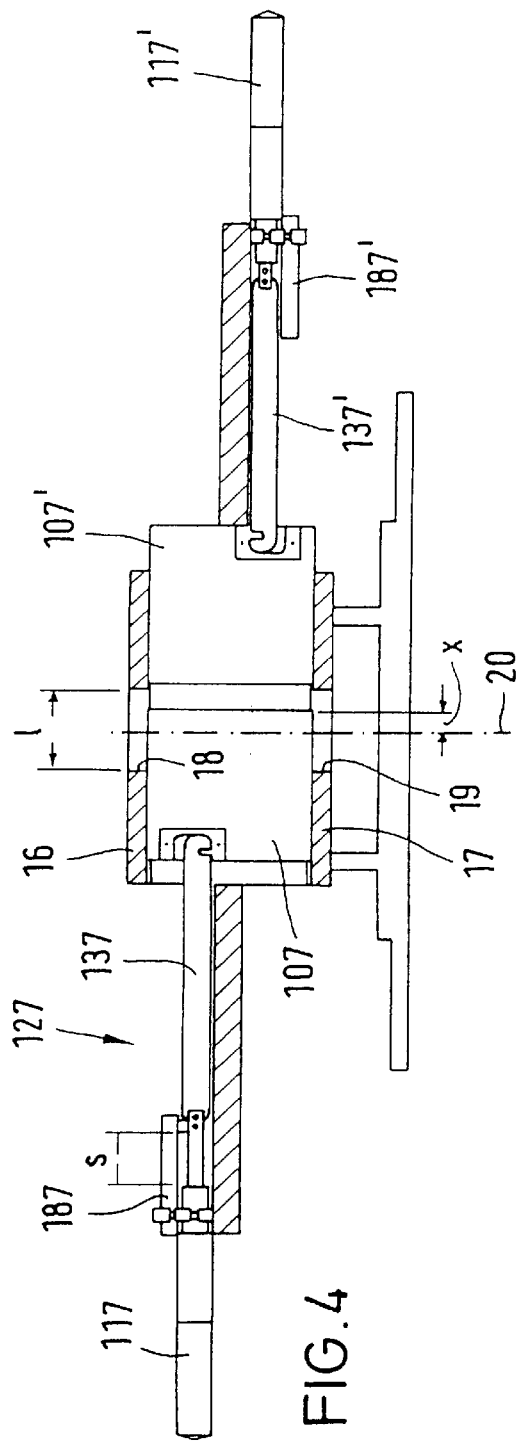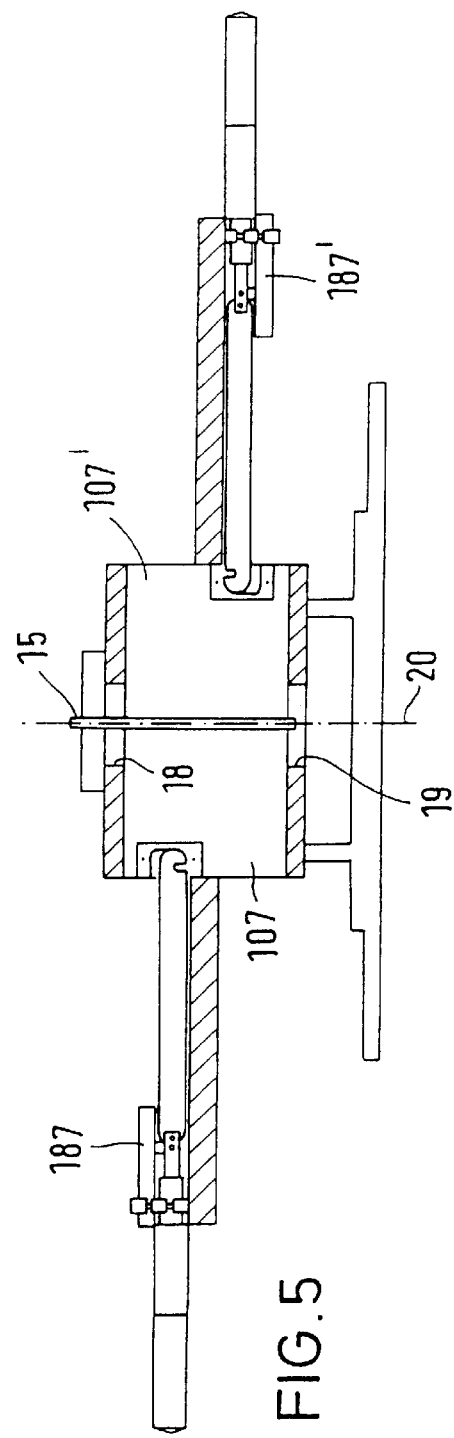

CONTOUR COLLIMATOR FOR RADIOTHERAPY

This invention relates to a contour collimator for radiotherapy, comprising a plurality of plate-shaped diaphragm elements movably arranged with respect to each other in a guiding block to form a contour diaphragm for a radiation beam emitted by a radiation source towards the collimator, and at least one drive for moving the diaphragm elements.

Such a contour collimator is known from EP 0 387 921 B1. In radiotherapy, such contour collimators serve for forming a diaphragm whose opening corresponds to the contour of the area of the human body to be irradiated, so that the high-energy rays emanating from the radiation source only impinge on this area and the surroundings of this area are shielded from the radiation.

The known contour collimator provides for each group of a given number of plate-shaped diaphragm elements a common adjusting part which serves for serially moving one select diaphragm element each relative to the remaining diaphragm elements. For this purpose, a gear of the adjusting part meshes with a rack provided at the diaphragm element and a non-rotary, toothed area of the adjusting part meshes with the rest of the diaphragm elements to fix them. In order to accelerate the adjusting step, the prior art proposes to provide two such adjusting parts on either side of the contour collimator.

For moving the individual diaphragm elements, the prior art makes necessary that the respective adjusting part is initially moved translatorily and transversely to the diaphragm elements, so that the adjusting gear comes into engagement with the rack of a select diaphragm element. Then, a rotation is applied to the gear to move the associated diaphragm element. This process has to be repeated for each diaphragm element of a group.

It is the object of the present invention to create a contour collimator of the generic kind, which can be adjusted more rapidly and altogether has a simpler and thus operationally more reliable design requiring less maintenance.

According to the characterizing part of claim 1 this object is achieved in that a drive is associated with each diaphragm element, that the drives of one group of diaphragm elements are substantially adjacent to one another and that a driving transmission is provided between each drive and the associated diaphragm element.

In spite of the distance which is laterally very narrow between the individual diaphragm elements and corresponds approximately to the thickness of a diaphragm, e.g. 1 mm, it is possible with this design to equip each diaphragm element with a drive of its own thus actuating it separately. This serves for considerably accelerating the adjusting time for a contour collimator, so that the irradiation time for each patient is reduced in one respect, which is a relief for the patient and is also simultaneously accompanied by an increase in economic efficiency.

In an advantageous embodiment, the drives are arranged substantially as a semicircle. This serves for obtaining an especially simple and clearly arranged design in which the driving transmissions have substantially equal length, so that equal components can be used for the design.

In a further advantageous embodiment, each driving transmission has a flexible towards tension-resistant and pressure-resistant power-transmitting element, one end of which is connected with the associated diaphragm element and the other end of which is connected with the associated drive and which is movably supported in translatory fashion in a moving guide. Such a power-transmitting element permits an especially flexible arrangement of the drives.

When each power-transmitting element is detachably coupled to its associated diaphragm element via a coupling linkage, this creates a simple design of the contour collimator, which also permits the rapid exchange of individual elements without any difficulties.

The same advantage occurs when each power-transmitting element is detachably coupled to its associated drive via a coupling linkage.

Each power-transmitting element advantageously comprises a spring band.

Each drive is preferably formed by a linearly acting motor. This renders possible an especially slim or narrow design of the arrangement of drives, so that the arrangement of drives can be very compact.

In this connection, the motor is preferably an electric linear motor.

As an alternative, the motor is an electric motor having a linearly acting gearing, preferably a rack-and-pinion gear or a spindle gearing.

When the guiding block has upper and lower guide plates each of which is provided with a plurality of upper guide grooves and lower guide grooves, respectively, for the diaphragm elements, an especially reliable and fail-safe adjustability of the diaphragm elements is guaranteed.

In a preferred embodiment, the upper and lower guide plates are each provided with a preferably rectangular opening, which determine the maximum diaphragm opening and have a common middle plane extending substantially rectangularly with respect to the longitudinal direction of the guide grooves.

When the moving guides are arranged substantially side by side in a moving guide block and have moving guide gaps which diverge in bent and fan-shaped fashion and each of which accommodates a power-transmitting element in translatorily movable fashion, safe guidance of the power-transmitting elements is achieved, so that an accurate translatory adjustment of the diaphragm elements is possible, since undesired bulging of the power-transmitting elements is prevented by the gap walls tightly abutting against the respective power-transmitting element.

An especially compact arrangement will be formed when two superposed planes of drive arrangements are associated with each moving guide block, two superposed drives each being applied to one power-transmitting element accommodated in contiguous moving guides. By this, the overall width of the contour collimator can be limited effectively in spite of a plurality of movable diaphragm elements.

When two opposite groups of translatorily drivable diaphragm elements are provided in the guiding block, two opposite diaphragm elements each being guided in upper and lower common guide grooves, on the one hand, the provision of the opposite groups of diaphragm elements creates the possibility of adjusting contours rotating about an angle of 360° and, on the other hand, it is made possible to achieve complete screening in the area of said guide groove by contact of two opposite diaphragm elements.

When each diaphragm element of a pair of opposite diaphragm elements is movable with its free edge facing away from the respective drive beyond the common middle plane of the openings in the lower and upper guide plates, contours can be produced which have strong constrictions on one side as is the case e.g. with kidney-shaped contours.

It is preferred to associate with each drive a displacement pickup, preferably a potentiometer, for detecting the current position of the corresponding diaphragm element.

This serves for enabling an accurate control of the diaphragm element positions, so that e.g. the contour can automatically be adjusted by a computer program.

This embodiment is especially reliable and inexpensive when the displacement pickup has a moving potentiometer which can be actuated translatorily.

If at least one of the diaphragm elements disposed within the region of the central middle ray of the radiation beam is provided with at least one thickening rib extending in the translational direction, reliable shading of the central middle ray will be achieved, since the thickening rib shades the middle ray extending parallel to the diaphragm element. As an alternative, the diaphragm elements can be inclined towards the ray. Moreover, the top of a middle diaphragm element can alternatively be thicker than its bottom.

This shading effect is even intensified when each thickening rib meshes with a corresponding groove in the adjacent diaphragm element.

The invention is explained in more detail below with reference to the drawing by means of an example; wherein FIG. 1 is a perspective top view onto a contour collimator according to the invention;

FIG. 2A is a partial view of a guiding block, which is broken away, with some diaphragm elements being inserted;

FIG. 2B is a side view of a guiding block in the translational direction of the diaphragm elements;

FIG. 2C is a section of FIG. 2B, which shows the diaphragm elements inserted in the guide rails in the region of the lower guide plate;

FIG. 3 is a perspective top view onto a second embodiment of a contour collimator which is provided with displacement pickups;

FIG. 4 is a sectional view through a contour collimator corresponding to the longitudinal middle plane IV—IV in FIG. 3, indicated in dash-and-dot lines, in a first position of the diaphragm elements;

FIG. 5 is a sectional view corresponding to the section in FIG. 4 in a calibration position of the diaphragm elements;

Figure 1:
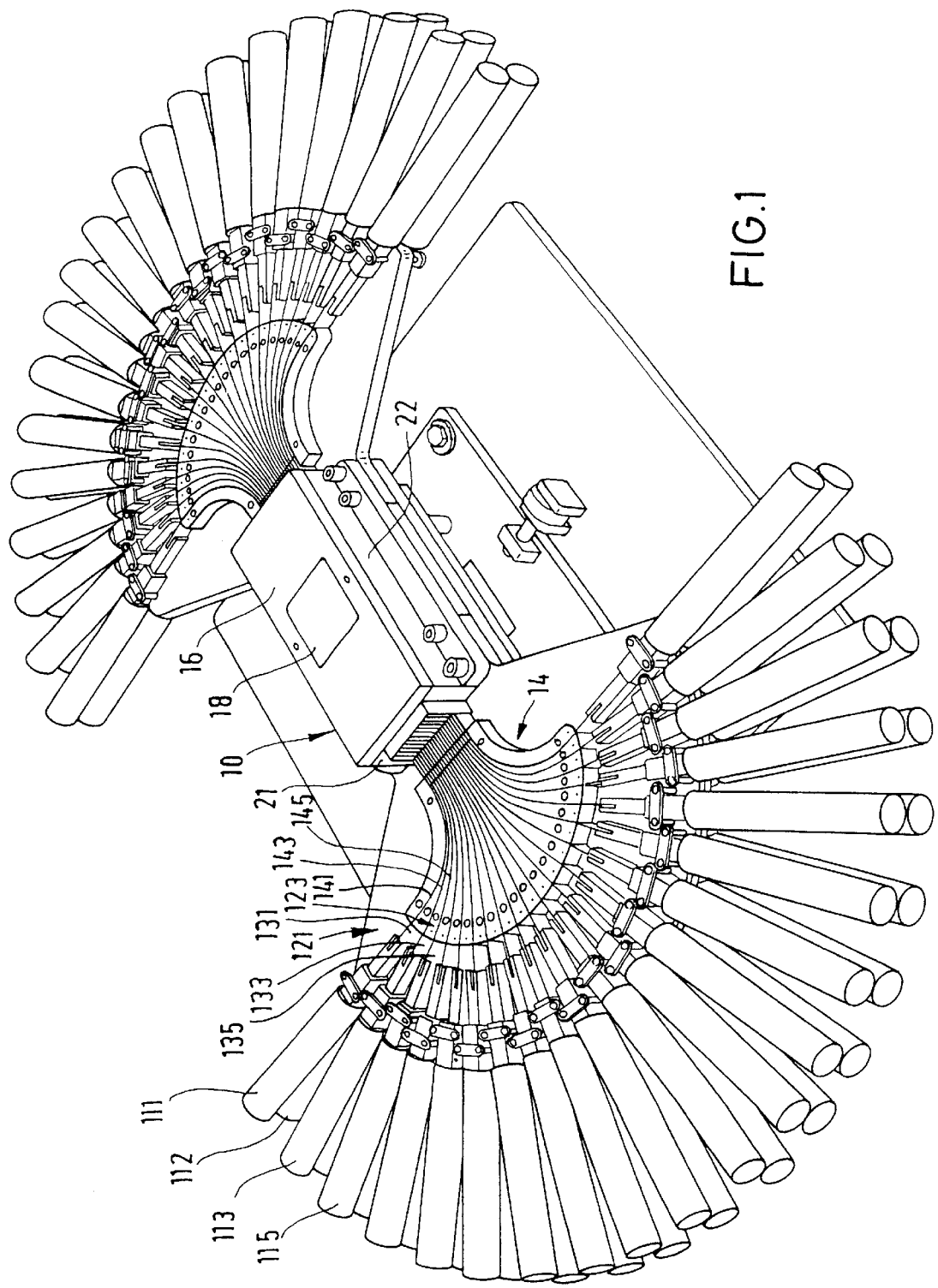
FIG. 1 is a perspective view of a contour collimator according to the invention whose core is formed by a guiding block 10 which is illustrated in detail in FIGS. 2A to 2C.

The guiding block 10 has a lower guide plate 17, an upper guide plate 16 as well as two side walls 21 and 22. A substantially rectangular opening 18 is provided centrally in the upper guide plate 16. A lower opening 19 which is in substantially vertical alignment with the upper opening 18 is provided centrally in the lower guide plate 17. The top side of the lower guide plate 17 is provided with a plurality of lower guide grooves 171, 172, 173, . . . extending in the longitudinal direction of the lower guide plate 17 and formed parallel to one another at equal lateral distance and on one side of the lower opening 19. The upper and lower guide plates 16, 17 are made preferably of brass, bronze or ceramics or a radiation-resistant material having good sliding properties.

Further lower guide grooves 171', 172', 173', . . . are developed on the other side of the lower opening 19 in alignment with the lower guide grooves 171, 172, 173, . . . In the same way, upper guide grooves 161, 162, 163, . . . and further upper guide grooves (not shown) which are in alignment with the guide grooves 161, 162, 163, . . . and are formed on the other side of the upper opening 18 are provided on the bottom side of the upper guide plate 16.

Since the guiding block 10 is made symmetrically with respect to the middle plane 20 extending rectangularly relative to the guide grooves 161, 162, 163, . . . ; 171, 172, 173, . . . ; 171', 172', 173', . . . and through the center of openings 18 and 19, only the design of the guiding block on one side with respect to the middle plane 20 is described below for the purpose of simplification. The design on the other side is formed analogously thereto.

A plate-shaped diaphragm element 101; 102; 103; . . . is inserted in movably translatory fashion in each pairing of the vertically superposed guide grooves 161, 171; 162, 172; 163, 173; . . .

As is evident from FIG. 2C, the width of the individual guide grooves 161, 171, . . . corresponds to about half the thickness of a diaphragm element 101, . . . , the thickness of a plate-shaped diaphragm element being about 1 mm. A ridge 171" is formed between two adjacent guide grooves 171, 172. Its width is somewhat greater than the width of the adjacent guide grooves 171, 172 and thus also somewhat greater than half the width of a diaphragm element. Each diaphragm element has a section 101" of reduced thickness at its lower edge, which section is inserted in its associated guide groove 171 and is translatorily movable therein. Although an analogously developed upper section of reduced thickness which engages the guide groove 161 is not shown in the drawing, the upper edges of the diaphragm elements 101, 102, 103, . . . as well as the upper guide plate in the region of the upper guide grooves 161, 162, 163, . . . are developed analogously to the lower edges of the diaphragm elements 101, 102, 103, . . . and the lower guide plate 17 in the region of its guide groove 171, 172, 173, . . . , as illustrated in FIG. 2C.

Because of the differing widths of the guide grooves 171, 172, 173 and the ridges 171", 172" disposed therebetween, the diaphragm elements 101, 102 inserted in the guide grooves 171, 172 are slightly spaced laterally, so that they do not come into contact.

The diaphragm elements are provided with coupling linkages 154, 155 at their vertical edge facing away from the middle plane 20, as evident from FIG. 2A by means of plates 174 and 175. The coupling linkages 154, 155 are alternately developed in the vicinity of the lower guide plate 17 and the upper guide plate 16, so that they are displaced upwardly or downwardly in each case when the diaphragm elements are disposed side by side.

Figure 6:
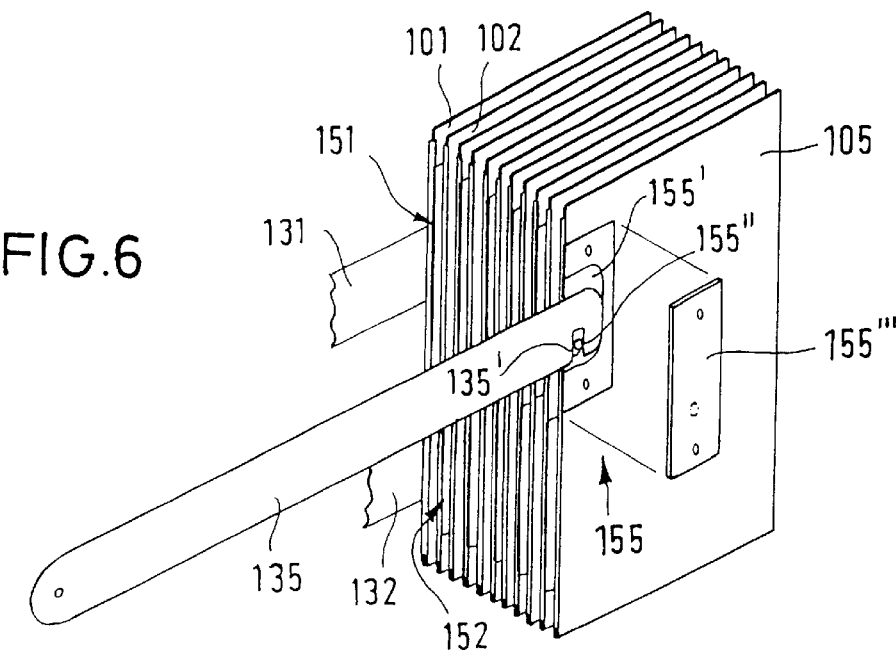
FIG. 6 is a view in which a power-transmitting element is mounted on a diaphragm element.

Such a coupling linkage is shown in more detail in FIG. 6 for the diaphragm element 105. The coupling linkage 155 comprises a stepped recess 155' located in one side of the diaphragm element 105. A pivot 155" is provided in the more recessed portion of the stepped recess 155', which is left untouched during the manufacture of the recess and which corresponds to the full thickness of the diaphragm element 105. This recess 155' is produced by milling out the surface of the metallic diaphragm element which is preferably made of tungsten.

The more recessed region of the stepped recess has such a dimension that a hook-like recess 135' of a power-transmitting element 135 can be inserted in this more recessed region and grips behind the pivot 155". In this case, the thickness of the power-transmitting element corresponds approximately to the height of the step within the stepped recess 155' and is preferably 0.30 mm, while the height of the power-transmitting element is about 13 mm. The power-transmitting element 135 consists preferably of spring steel.

After inserting a cover plate 155''' in the less recessed region of the stepped recess 155' and anchoring it, the power-transmitting element 135 with its hook-like recess 135' is suspended in the more recessed portion of the stepped recess 155', the pivot 155'' being thus gripped behind. This prevents the power-transmitting element 135 from laterally falling out. In this way, a particulated coupling linkage 155 is formed between the diaphragm element 105 and the power-transmitting element 135.

Each of the flexible but tension-resistant and pressure-resistant power-transmitting elements 131, 132, 133, . . . , 135, . . . , made of spring steel, is accommodated in an upper moving guide and lower moving guide, respectively. FIG. 1 only shows the upper moving guides 141, 143, 145. The moving guides for the power-transmitting elements which are associated with the diaphragm elements 102, 104, . . . whose lower regions are provided with the coupling linkage, are arranged underneath the moving guides shown in FIG. 1 in a plane which is disposed underneath.

Like those of the plane disposed underneath—the moving guides 141, 143, 145, . . . are arranged in outwardly bent and fan-shaped fashion, the radius of curvature of the moving guides decreasing outwardly, which means that the radius of curvature of the moving guides 141 is less for the power-transmitting element 133 of the diaphragm element 101 placed closer to the side wall 21, i.e. the curvature is greater than the radius of curvature for a power-transmitting element of a diaphragm element located more closely towards the middle. On the other side, i.e. towards the other side wall 22, the radius of curvature of the moving guides decreases again, so that there the curvature increases again. In this way, the power-transmitting elements are fanned at an angle of about 180° as shown in FIG. 1.

At their fanned, free ends, the power-transmitting elements 131, 132, 133, . . . , 135, . . . are each coupled to a drive 111, 112, 113, . . . , 115, . . . developed as a linear drive. Thus, driving transmissions 121, 122, . . . , 125, . . . for transmitting the linear motion produced by the respective drive to the associated diaphragm element are created by this coupling between the respective drive 111, 112, 113, . . . , 115, . . . with the power-transmitting element 131, 132, 133, . . . , 135, . . . , the coupling linkage 151, 152, . . . , 155, . . .
ba with the respective diaphragm element 101, 102, . . . , 105, . . .

The fanning, shown in FIG. 1, of the individual driving transmissions 121, 122, . . . permits in an especially advantageous manner the arrangement of a plurality of drives 111, 113, 115, . . . side by side on the most confined space, the arrangement shown in FIG. 1, of the drives in two superposed planes, increasing the compactnessas again as illustrated by means of drives 111 and 112.

Correspondingly, in the example shown in FIG. 1 the odd diaphragm elements—when the diaphragm elements located side by side are numbered—are provided in their upper region with the coupling linkage to which the respective power-transmitting element is coupled which extends to an upper row of drives via an upper fan-shaped arrangement of moving guides, while the lower region of the even diaphragm elements include the coupling linkage which pivots them to the power-transmitting elements, which extends through a lower fan-shaped arrangement of moving guides to a lower row of drives. This arrangement makes possible to attach a very large number of extremely narrow diaphragm elements closely side by side and apply a drive of its own to each of them.

An alternative embodiment of the arrangement shown in FIG. 1 is illustrated in FIG. 3, only few reference numerals being entered for the purpose clarity. A displacement pickup 181, 183 is associated with each driving transmission 121, 123 in the region of the associated drive 111, 113, which measures the degree of translatory movement and passes it on to a control circuit. The position of each individual diaphragm element 101, 103, . . . can be determined by these displacement pickups 181, 183, . . . which are preferably formed by sliding potentiometers, so that a computer-controlled precise contour can be adjusted in the collimator.

FIG. 4 shows a contour collimator according to the invention in a longitudinal section, a front diaphragm element 107 of a first group of diaphragm elements, driven by a drive 117 via the driving transmission 127 including the power-transmitting element 137, being moved to a position in which the free edge of the diaphragm element 107, located in the region of the openings 18 and 19 in the upper guide plate and the lower guide plate 17, respectively, projects from the middle plane 20, so that the diaphragm element 107 shades over 50% of the longitudinal extension of the opening 18 and 19, respectively. The opposite diaphragm element 107' of a second group has been retracted from its drive 117' via its power-transmitting element 137' to such an extent that its free edge facing the openings 18, 19 has come out of the cross-section of the openings 18 and 19, respectively.

Thus, as shown in the case of the associated displacement pickup 187 the possible travel s of the driving transmission 127 is greater than the longitudinal extension l of the opening 18 and 19, respectively, by the amount of x. This renders possible to produce contours with the contour collimator according to the invention, which have strong constrictions on one side, as is the case e.g. with kidney-shaped contours.

A position of the diaphragm elements 107, 107' is shown in FIG. 5, in which the respective free edge of the diaphragm elements 107, 107', disposed in the region of the openings 18, 19, abut against a calibration plate 15 extending vertically through the openings 18, 19 and fixed centrally in the middle plane 20. In this position, both diaphragm elements 107, 107' are located symmetrically with respect to the middle plane 20, so that either the associated displacement pickups 187, 187' can be positioned symmetrically in the setting shown in FIG. 5 or the signals applied by these displacement pickups 187, 187' can be stored in a control unit as symmetry reference signals.

Figure 7:
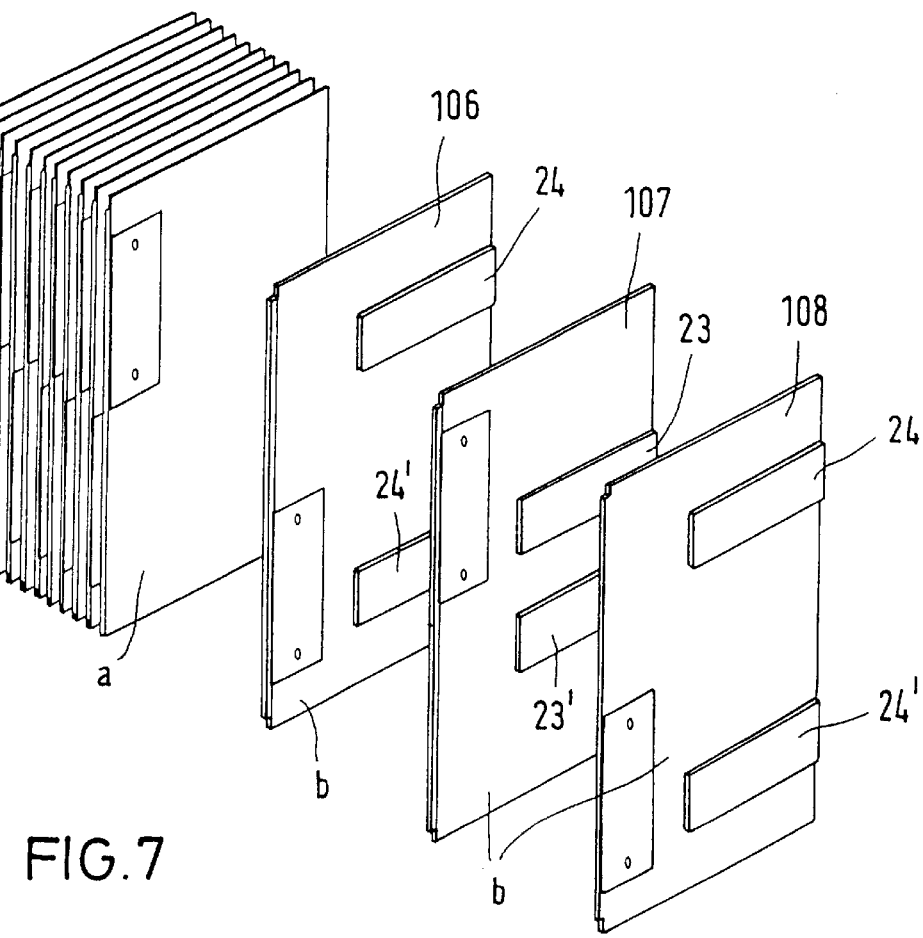
FIG. 7 shows different diaphragm elements with and without thickening ribs.
Figure 8:
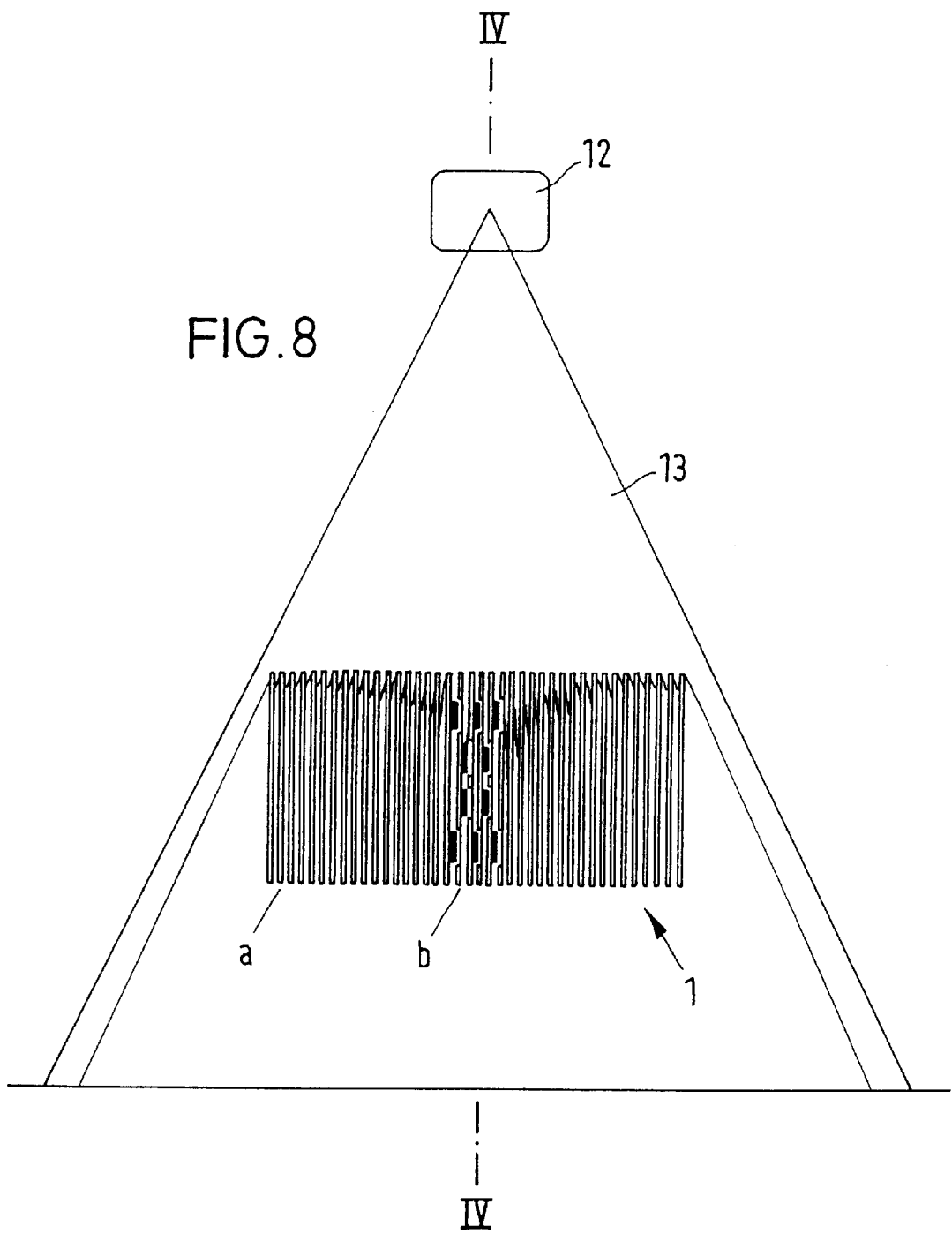
FIG. 8 is a diagram of the ray shading of a contour collimator according to the invention.

Differing kinds of diaphragm elements are shown in FIG. 7, the diaphragm elements referred to as a corresponding to those (101, 102, . . . , 105) which are dealt with and described above already. The diaphragm elements 106, 107, 108 referred to as b are made for use in the region of the longitudinal middle plane of the contour collimator, which is referred to as IV—IV in FIG. 3. As illustrated in FIG. 8, the center of the radiation source 12 is usually also located in this longitudinal middle plane, from which source the radiation beam 13 is directed conically downwardly towards the collimator 1.

If type a diaphragm elements were arranged in the region of the longitudinal middle plane IV—IV, the middle ray emitted from the radiation source 12 and the rays directly adjacent thereto would pass through the intermediate spaces of the diaphragm elements in almost unimpeded and non-shaded fashion, so that the collimator would be ineffective in the vicinity of the longitudinal middle plane IV—IV. As shown in FIG. 7, the type b diaphragm elements arranged in the region of the longitudinal middle plane IV—IV are provided for this reason with thickening ribs 23, 23' and 24, 24', respectively. In this connection, the thickening ribs extend in the direction of the translational motion of the respective diaphragm elements and over the entire length or at least over more than 50% of the length of the respective diaphragm element in the translational direction.

The respective thickening ribs 23, 23'; 24, 24' mesh with correspondingly shaped grooves (not shown) on the opposite side of the adjacent diaphragm element, so that the gap between two adjacent diaphragm elements is interrupted by the respective thickening elements in radiation-shielded fashion. In this way, the passage of the middle ray and the rays adjacent thereto, respectively, is effectively prevented by the gap formed between the type b diaphragm elements as illustrated in FIG. 8.

In order to prevent an attenuation of the material of the adjacent type b diaphragm elements in the region of the grooves and the thickenings, the thickenings 23, 23' and 24, 24', respectively, of two adjacent type b diaphragm elements as well as the associated grooves provided therein are displaced over the height of the respective diaphragm element, as illustrated in FIG. 7.

What is claimed is:

1. A contour collimator for radiotherapy, comprising a plurality of plate-shaped diaphragm elements provided in a guiding block and movably arranged with respect to one another to form a contour diaphragm for a radiation beam emitted by a radiation source towards the collimator, and comprising at least one drive for moving the diaphragm elements, wherein a drive of its own is associated with each diaphragm element, the drives of a group of diaphragm elements are arranged substantially adjacent to one another, and a driving transmission of its own is provided between each drive and the associated diaphragm element, wherein the drives are arranged substantially in a semi-circle.

2. The contour collimator according to claim 1, wherein at least one displacement pickup for detecting the position of the corresponding diaphragm element is associated with each drive.

3. The contour collimator according to claim 1, wherein each driving transmission has a flexible but tension-resistant and pressure-resistant power-transmitting element one end of which is connected with the associated diaphragm element and the other end of which is connected with the associated drive and which is supported in a moving guide in translatorily movable fashion.

4. The contour collimator according to claim 3, wherein each power-transmitting element is detachably coupled to the associated diaphragm element via a coupling linkage.

5. The contour collimator according to claim 3, wherein each power-transmitting element is detachably coupled to the associated drive via a further coupling linkage.

6. The contour collimator according to claim 3, wherein each power-transmitting element has a spring band.

7. The contour collimator according to claim 1, wherein each drive comprises a linearly acting motor.

8. The contour collimator according to claim 7, wherein the motor is an electric linear motor.

9. The contour collimator according to claim 7, wherein the motor is an electric motor having a linearly acting gearing selected from the group consisting of a rack-and-pinion gear and a spindle gearing.

10. The contour collimator according to claim 1, wherein the guiding block has upper and lower guide plates which are each provided with a plurality of upper guide grooves and lower guide grooves, respectively, for the diaphragm elements.

11. The contour collimator according to claim 10, wherein the upper and lower guide plates are each provided with a rectangular opening which determine the maximum diaphragm opening and have a common middle plane extending substantially rectangularly with respect to the longitudinal direction of the guide grooves.

12. A contour collimator for radiotherapy, comprising a plurality of plate-shaped diaphragm elements provided in a guiding block and movably arranged with respect to one another to form a contour diaphragm for a radiation beam emitted by a radiation source towards the collimator, and comprising at least one drive for moving the diaphragm elements, wherein a drive of its own is associated with each diaphragm element, the drives of a group of diaphragm elements are arranged substantially adjacent to one another, and a driving transmission of its own is provided between each drive and the associated diaphragm element, wherein each driving transmission has a flexible but tension-resistant and pressure-resistant power-transmitting element one end of which is connected with the associated diaphragm element and the other end of which is connected with the associated drive and which is supported in a moving guide in translatorily movable fashion, and wherein the moving guides are arranged substantially side by side in a moving guide block and have moving guide gaps diverging in fan-shaped and bent fashion, in which one power-transmitting element is accommodated in translatorily movable fashion.

13. A contour collimator for radiotherapy, comprising a plurality of plate-shaped diaphragm elements provided in a guiding block and movably arranged with respect to one another to form a contour diaphragm for a radiation beam emitted by a radiation source towards the collimator, and comprising at least one drive for moving the diaphragm elements, wherein a drive of its own is associated with each diaphragm element, the drives of a group of diaphragm elements are arranged substantially adjacent to one another, and a driving transmission of its own is provided between each drive and the associated diaphragm element, wherein two superposed planes of drive arrangements are associated with each moving guide block, on power-transmitting element, accommodated in adjacent moving guides, being applied by two superposed drives each.

14. The contour collimator according claim 1, wherein two opposite groups of tanslatorily drivable diaphragm elements are provided in the guiding block, two opposite diaphragm elements each being guided in lower and upper common guide grooves.

15. The contour collimator according to claim 1, wherein each diaphragm element of a pair of opposite diaphragm elements is movable with its free edge facing away from the respective beyond the common middle plane of openings in upper and lower guide plates.

16. The contour collimator according to claim 12, wherein the displacement pickup comprises a potentiometer.

17. The contour collimator according to claim 2, wherein the displacement pickup comprising a moving potentiometer which can be actuated translatorily.

18. A contour collimator for radiotherapy, comprising a plurality of plate-shaped diaphragm elements provided in a guiding block and movably arranged with respect to one another to form a contour diaphragm for a radiation beam emitted by a radiation source towards the collimator, and comprising at least one drive for moving the diaphragm elements, wherein a drive of its own is associated with each diaphragm element, the drives of a group of diaphragm elements are arranged substantially adjacent to one another, and a driving transmission of its own is provided between each drive and the associated diaphragm element, wherein at least one of the diaphragm elements located in the region of the central middle ray of the radiation beam is provided with at least one thickening rib extending in the translational direction.

19. The contour collimator according to claim 18, wherein each thickening rib engages a corresponding groove in the adjacent diaphragm element.

* * * * *

UNITED STATES PATENT AND TRADEMARK OFFICE
CERTIFICATE OF CORRECTION

PATENT NO. : 6,188,748 B1
DATED : February 13, 2001
INVENTOR(S) : Otto Pastyr, Wolfgang Schlegel, Karl-Heinz Hover, Wolfgang Maier-Borst It is certified that error appears in the above-identified patent and that said Letters Patent is hereby corrected as shown below:

Column 5,
Line 43, delete "ba"

Column 6,
Line 27, change "s" to -- $\underline{s}$ --.
Line 47, change "a" to -- $\underline{a}$ --
Line 50, change "b" to -- $\underline{b}$ --.
Line 57, change "a" to -- $\underline{a}$ --.
Line 64, change "b" to -- $\underline{b}$ --.

Column 7,
Line 12, change "b" to -- $\underline{b}$ --.
Line 15, change "b" to -- $\underline{b}$ --.
Line 17, change "b" to -- $\underline{b}$ --.

Column 8,
Line 42, change "according claim" to -- according to claim --.
Line 50, change "respective beyond" to -- respective drive beyond --.
Line 55, change "comprising" to -- comprises --.

Signed and Sealed this

Sixteenth Day of October, 2001

Attest:

NICHOLAS P. GODICI
Attesting Officer    Acting Director of the United States Patent and Trademark Office